US010744259B2

United States Patent
Yagi (10) Patent No.: US 10,744,259 B2
(45) Date of Patent: Aug. 18, 2020

(54) INFUSION STATE DETECTION SYSTEM

(71) Applicant: TERUMO KABUSHIKI KAISHA, Tokyo (JP)

(72) Inventor: Akihiko Yagi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 153 days.

(21) Appl. No.: 15/706,213

(22) Filed: Sep. 15, 2017

(65) Prior Publication Data
US 2018/0001022 A1    Jan. 4, 2018

Related U.S. Application Data

(63) Continuation of application No. PCT/JP2016/052098, filed on Jan. 26, 2016.

(30) Foreign Application Priority Data

Mar. 17, 2015    (JP) .................. 2015-053805

(51) Int. Cl.
*A61M 5/168*    (2006.01)
*A61J 1/10*    (2006.01)
*A61M 5/142*    (2006.01)

(52) U.S. Cl.
CPC ........ *A61M 5/16859* (2013.01); *A61M 5/168* (2013.01); *A61M 5/16854* (2013.01); *A61J 1/10* (2013.01); *A61M 5/14232* (2013.01); *A61M 2005/16863* (2013.01); *A61M 2005/16868* (2013.01); *A61M 2205/15* (2013.01); *A61M 2205/18* (2013.01); *A61M 2205/3334* (2013.01); *A61M 2205/3344* (2013.01);
(Continued)

(58) Field of Classification Search
CPC .......... A61M 5/16859; A61M 5/16854; A61M 5/16831; A61M 5/142; A61M 5/172; A61M 5/16836; A61M 2205/3334; A61M 2205/16868; A61M 2205/15; A61M 2005/16863
USPC ....................................................... 604/111
See application file for complete search history.

(56) References Cited

U.S. PATENT DOCUMENTS 9,427,521 B2 *   8/2016   Pope ................... A61M 5/5086
2010/0262078 A1   10/2010   Blomquist
(Continued)

FOREIGN PATENT DOCUMENTS

JP    3551974    8/2004
JP    2005-278766    10/2005
(Continued)

OTHER PUBLICATIONS

International Search Report issued in International Patent Application No. PCT/JP2016/052098 dated Mar. 8, 2016.

*Primary Examiner* — Brandy S Lee
*Assistant Examiner* — Nidah M Hussain
(74) *Attorney, Agent, or Firm* — Foley & Lardner LLP (57) ABSTRACT

An infusion state detection system includes: a pump unit configured to deliver a liquid in an infusion line; a pressure detector configured to detect a pressure in the infusion line; and a determination processing unit configured to: when the pressure detected by the pressure detector is at a predetermined value or above, stop driving of the pump unit for a stop period, and determine an infusion state on the basis of a value of the pressure detected by the pressure detector during the stop period.

6 Claims, 7 Drawing Sheets

(52) U.S. Cl.
CPC ... *A61M 2205/50* (2013.01); *A61M 2205/502* (2013.01); *A61M 2205/581* (2013.01); *A61M 2205/8206* (2013.01)

(56) References Cited

U.S. PATENT DOCUMENTS

| | | | | |
|---|---|---|---|---|
| 2011/0009817 | A1* | 1/2011 | Bennett | A61M 5/168 604/93.01 |
| 2011/0142688 | A1 | 6/2011 | Chappel et al. | |
| 2012/0059313 | A1 | 3/2012 | Shergold | |
| 2013/0310743 | A1* | 11/2013 | Yagi | A61M 5/16836 604/111 |
| 2014/0147246 | A1 | 5/2014 | Chappel et al. | |
| 2014/0378898 | A1* | 12/2014 | Rosinko | A61M 5/16836 604/111 |
| 2015/0005732 | A1* | 1/2015 | Halbert | A61M 5/16854 604/500 |

FOREIGN PATENT DOCUMENTS

| | | |
|---|---|---|
| JP | 2012-506279 | 3/2012 |
| JP | 2012-522583 | 9/2012 |
| JP | 2014-526008 | 10/2014 |
| WO | WO-98/04304 | 2/1998 |
| WO | WO-2012/042710 | 4/2012 |

* cited by examiner

EXTRAVASATION PHENOMENON

FIG. 4B

BLOCKAGE PHENOMENON

INFUSION STATE DETECTION SYSTEM

CROSS-REFERENCE TO RELATED APPLICATIONS

The present application is a bypass continuation of PCT Application No. PCT/JP2016/052098, filed on Jan. 26, 2016, which claims priority to Japanese Application No. 2015-053805, filed on Mar. 17, 2015, the contents of which are hereby incorporated by reference in their entireties.

BACKGROUND

The present application relates to an infusion state detection system configured to detect an abnormality in an infusion state when a liquid such as a medicinal solution is delivered using an infusion line.

The infusion line is formed by connecting an infusion set such as a medical bag, a tube, and an indwelling needle, for treatment of continuously administering a medicinal solution to a patient with an arbitrary supply amount. This type of treatment demands ensured conduction in the infusion line and stable delivery of the medicinal solution. Generally, an infusion pump includes a pressure sensor for detecting the pressure in the infusion line and an abnormality (occurrence of occlusion) of a conduction state in the infusion line is detected on the basis of a pressure value detected by the sensor.

Meanwhile, potential adverse events during infusion include an extravasation, that is, leakage of the medicinal solution into the subcutaneous tissue between the blood vessel and the epidermis as a result of a dislocated indwelling needle of the infusion line from the blood vessel into which the needle is inserted. In this case, even though the pressure inside the infusion line increases because the medicinal solution is pushed into the subcutaneous tissue, this degree of increase is smaller than a case where the infusion line is completely occluded, and thus, it is difficult to detect the increase with a sensor attached to the infusion pump in many cases. Moreover, there may be a case where the pressure increase due to extravasation is substantially equal to the degree of a pressure change induced by a posture change (standing up, etc.) of the patient, venous pressure fluctuation, or the like. Therefore, it difficult to determine the infusion state merely by monitoring the pressure in the infusion line during infusion. This leads to an unfavorable case, in the infusion state detection system, where reliability of detection is lowered due to an occurrence of misreporting, overlooking of the extravasation, or the like.

As a technique for solving these problems, a system disclosed in JP 3551974 B changes the flow rate of the medicinal solution during infusion and detects a pressure change accompanying the flow rate change, thereby distinguishing the liquid delivery resistance of the infusion line and the pressure change due to other factors so as to grasp the infusion state.

SUMMARY

The system disclosed in JP 3551974 B, however, the flow rate is changed during the administration of a medicinal solution, and thus, it is difficult to use the system in the administration of a medicine that needs strict flow rate control.

The concepts described in this application have been developed in view of the above circumstances, and are intended to provide an infusion state detection system capable of delivering liquid at a constant flow rate during infusion, and capable of determining the infusion state with high accuracy, thereby achieving higher reliability of detection with further enhanced usability.

An infusion state detection system according to one embodiment includes: a pump unit configured to deliver a liquid in an infusion line; a pressure detector arranged in the infusion line and configured to detect a pressure in the infusion line; and a determination processing unit configured to stop driving of the pump unit and determine an infusion state on the basis of a pressure value detected by the pressure detector during the stop period, in a case where the pressure value of the pressure detector becomes a predetermined pressure or above.

According to the above embodiment, the infusion state detection system can determine, with high accuracy, the infusion state using the pressure value of the pressure detector during the stop period of the pump unit. That is, the determination processing unit can satisfactorily estimate the leakage of the liquid to the outside of a living body lumen by detecting a sudden decrease in the pressure value during the liquid delivery stop period. With this configuration, the user can take necessary countermeasures at an early stage by receiving notification of the occurrence of liquid leakage. As a result, the infusion state detection system can achieve higher reliability of detection and further enhance usability. Moreover, with such a determination, it is possible to deliver the medicinal solution at a constant flow rate during the infusion, making it easier to control the supply of the liquid and to grasp the infusion state.

In one aspect, the determination processing unit measures a time at which the pressure value inside the infusion line during the stop period is a predetermined ratio of the predetermined pressure or below, and decides that the leakage of the liquid to the outside of the living body lumen has occurred in a case where the measured time is a predetermined period threshold or below.

That is, the liquid leakage to the outside of the living body lumen would lead to continuous discharge of the liquid, and this leads to sudden decrease in the pressure value during the stop period. Accordingly, the time measured by the determination processing unit is compared with the period threshold, and in a case where the measured time is the predetermined period threshold or below, it is possible to satisfactorily detect the leakage of the liquid to the outside of the living body lumen.

In another aspect, the determination processing unit decides that the leakage of the liquid to the outside of the living body lumen has occurred in a case where the pressure value at the time when a predetermined period threshold is passed from the time of becoming the liquid delivery stop state is a predetermined pressure determination threshold or below.

In this manner, by comparing, with the determination processing unit, the pressure value at the time when a predetermined period threshold is passed from the time of the liquid delivery stop state, with the pressure determination threshold, it is also possible to satisfactorily detect leakage of the liquid to the outside of the living body lumen.

In another aspect, the determination processing unit is configured to decide that the leakage of the liquid to the outside of the living body lumen has occurred in case where a change rate of the pressure value in the infusion line during the stop period is a predetermined change rate threshold or above.

In this manner, it is also possible to satisfactorily detect leakage of the liquid to the outside of the living body lumen by comparison by the determination processing unit of the change rate of the pressure value in the infusion line during the stop period with the change rate threshold.

In one aspect, the determination processing unit decides that occlusion of the infusion line has occurred in a case where driving of the pump unit is restarted after the end of the stop period and the pressure value detected by the pressure detector increases after the restart.

In this manner, it is possible to estimate that the occurrence of occlusion in the infusion line in a case where the pressure value detected by the pressure detector increases after the restart of driving of the pump unit. With this configuration, the user can take necessary countermeasures at an early stage by receiving notification of the occurrence of occlusion of the infusion line.

In one aspect, the pressure detector is arranged at a position in the vicinity of an insertion section of the infusion line to be inserted into the living body.

By arranging the pressure detector at a position in the vicinity of the insertion section of the infusion line in this manner, it is possible to detect the pressure value in the infusion line near the insertion section, leading to achieving determination of the infusion state by the determination processing unit with higher accuracy.

In one aspect, the determination processing unit is configured to automatically set the predetermined pressure on the basis of the liquid delivery amount of the pump unit.

With the configuration in which the determination processing unit automatically sets the predetermined pressure on the basis of the liquid delivery amount in this manner, it is possible to monitor the pressure change according to the liquid delivery amount, leading to further enhancement of the usability of the infusion state detection system.

According to certain embodiments described in this application, the infusion state detection system can deliver the liquid at a constant flow rate during the infusion and can determine the infusion state with high accuracy, thereby achieving higher reliability of the detection and further enhancing the usability.

DETAILED DESCRIPTION

Hereinafter, embodiments of the infusion state detection system will be described in detail with reference to the accompanying drawings.

Figure 1:
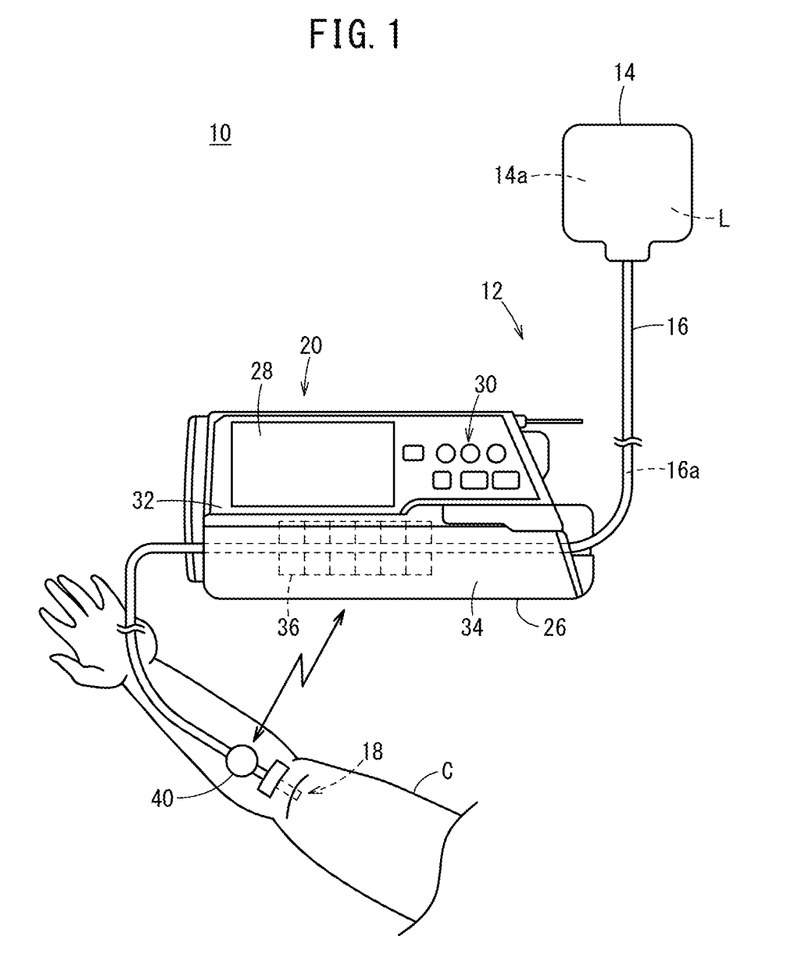
FIG. 1 is a diagram schematically illustrating an overall configuration of a liquid infusion state detection system according to one embodiment.

An infusion state detection system 10 according to one embodiment is applied to an infusion line 12 connected to the inside of the body of a patient C from a medical bag 14, as illustrated in FIG. 1. The infusion state detection system 10 is configured to determine an infusion state by detecting a pressure of a medicinal solution L (liquid) flowing inside of the infusion line 12. The infusion state detection system 10 continues infusion in a case where the infusion state is normal and gives warning to a medical practitioner, or the like, in a case where the infusion state is abnormal.

The infusion line 12 to which the infusion state detection system 10 is applied forms a flow path of the medicinal solution L to the patient C, and its components are not limited. FIG. 1 illustrates a representative case including the medical bag 14, a tube 16, an indwelling needle 18 (cannula) and a liquid delivery pump 20 (pump unit) are illustrated. The infusion line 12 may additionally include a drip tube, a klemme (clamp), a filter, a connector for connecting another tube 16. Moreover, the infusion state detection system 10 and the infusion line 12 may be provided collectively as an infusion set (product), or may be formed by arbitrarily combining components by the medical practitioner.

The medical bag 14 is formed in a bag shape by blow molding, or the like, using a thermoplastic resin material having flexibility and chemical resistance, and stores a predetermined amount of the medicinal solution L in an internal storage space 14a. One end of the tube 16 is connected to a lower end of the medical bag 14 via a needle for piercing a seal of a bottle (not illustrated), or the like. The medicinal solution L is discharged from the storage space 14a to the tube 16, thereby flowing inside the tube 16.

The medicinal solution L applied to the infusion solution is not particularly limited, and an appropriate one may be selected according to the disease or treatment details of the patient C. Examples of the medicinal solution L include an anticancer agent, an anesthetic agent, and a chemotherapeutic agent. Alternatively, the infusion line 12 may also be configured to deliver a liquid such as blood and a nutritional supplement other than the medicinal solution L.

The tube 16 is formed by injection molding from a thermoplastic resin material having flexibility and chemical resistance, and internally includes a conduit 16a for the medicinal solution L. In construction of the infusion line 12, the tube 16 is appropriately selected to have a sufficient length to connect from the medical bag 14 to the body surface of the patient C, with a margin. The infusion line 12 may be formed by connecting a plurality of tubes 16.

Figure 2:
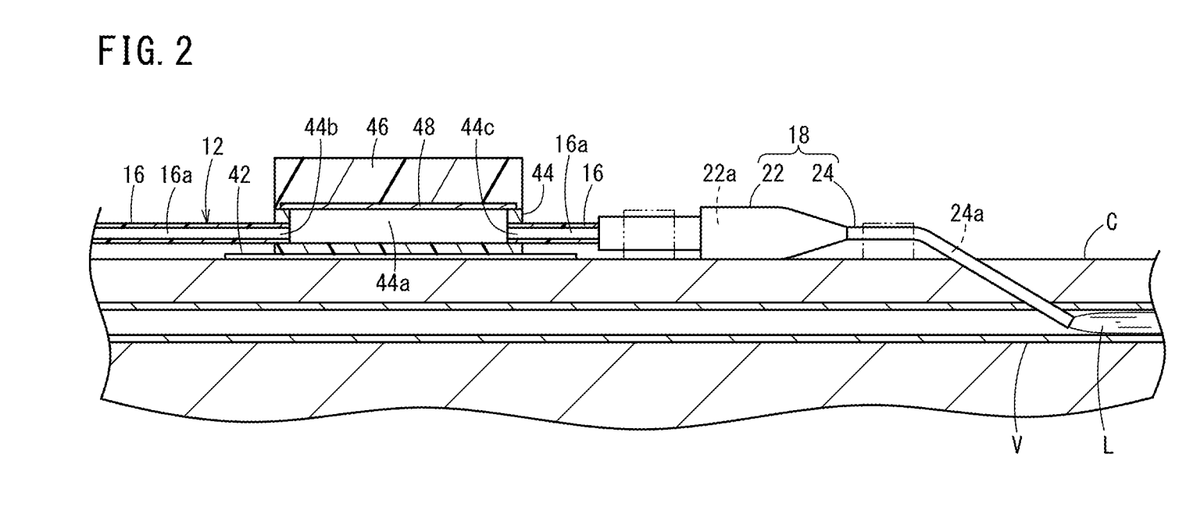
FIG. 2 is a partial sectional side view schematically illustrating a downstream side of the infusion line of FIG. 1.

The indwelling needle 18 is connected to an end of the tube 16 on the side opposite to the medical bag 14. As illustrated in FIG. 2, for example, the indwelling needle 18 includes a hub 22 functioning as a connector with the tube 16, and a small outside diametered tube 24 connected to the hub 22. The hub 22 is formed of a material harder than the tube 16, and internally includes a hollow portion 22a that communicates with the conduit 16a.

The small outside diametered tube 24 is formed of a flexible resin material and includes a discharge passage 24a communicating with the hollow portion 22a. The small outside diametered tube 24 is inserted into a blood vessel V (a vein as a living body lumen) from the body surface of the patient C together with a puncture needle (not illustrated) and is placed in the blood vessel V by removing the puncture needle. After being placed in the blood vessel V, the small outside diametered tube 24 allows the medicinal solution L to flow into the blood vessel V from a distal end opening of the tube via the discharge passage 24*a*. That is, the infusion line 12 includes the storage space 14*a*, the conduit 16*a*, the hollow portion 22*a*, and the discharge passage 24*a* as flow spaces for the medicinal solution L beginning from the medical bag 14 to the patient C. In the present description, these flow spaces are collectively referred to as the inside of the infusion line 12.

Returning to FIG. 1, the liquid delivery pump 20 is provided at a position in the middle of the tube 16 and includes a function of delivering the medicinal solution L at a constant flow rate into the blood vessel V. The liquid delivery pump 20 includes a liquid delivery unit 26 that houses a portion of the tube 16 to deliver the medicinal solution L, a display unit 28 that displays the display information necessary for delivering the medicinal solution L, and an operation unit 30 by which the medical practitioner operates the liquid delivery pump 20.

The liquid delivery unit 26 includes a main body unit 32 and a cover 34 and is configured such that the tube 16 can be set in the main body unit 32 in a state where the cover 34 is open. The main body unit 32 includes a groove (not illustrated) in which the tube 16 is arranged and a squeezing mechanism 36 is provided in this groove to squeeze the arranged tube 16. The squeezing mechanism 36 is formed with a plurality of pressing members (fingers in a case of a peristaltic type) and a plurality of rollers (not illustrated) (in a case of a roller type), for example, and sequentially presses the tube 16 from the upstream side toward the downstream side, thereby allowing the medicinal solution L present in the conduit 16*a* to flow toward the downstream side. The liquid delivery unit 26 delivers the medicinal solution L in the conduit 16*a* in the range of 0 mL to 999 mL, for example. Note that 0 mL is in the liquid delivery stop state.

The display unit 28 is a monitor that displays the liquid delivery amount of the medicinal solution L set by the user (medical practitioner such as a doctor or a nurse) or displays the liquid delivery amount of the medicinal solution L being actually delivered. The display unit 28 is formed with a liquid crystal display, for example. The display unit 28 also functions as the infusion state detection system 10 and displays the pressure inside the infusion line 12 detected during infusion, for example. Moreover, the display unit 28 may be configured to display warning in a case where an abnormality occurs in the infusion state.

The operation unit 30 is formed with a plurality of buttons and is capable of executing power on/off switching of the liquid delivery pump 20, drive start/stop switching of the liquid delivery pump 20, numerical changeover, setting, etc. of the liquid delivery amount, or the like.

Figure 3:
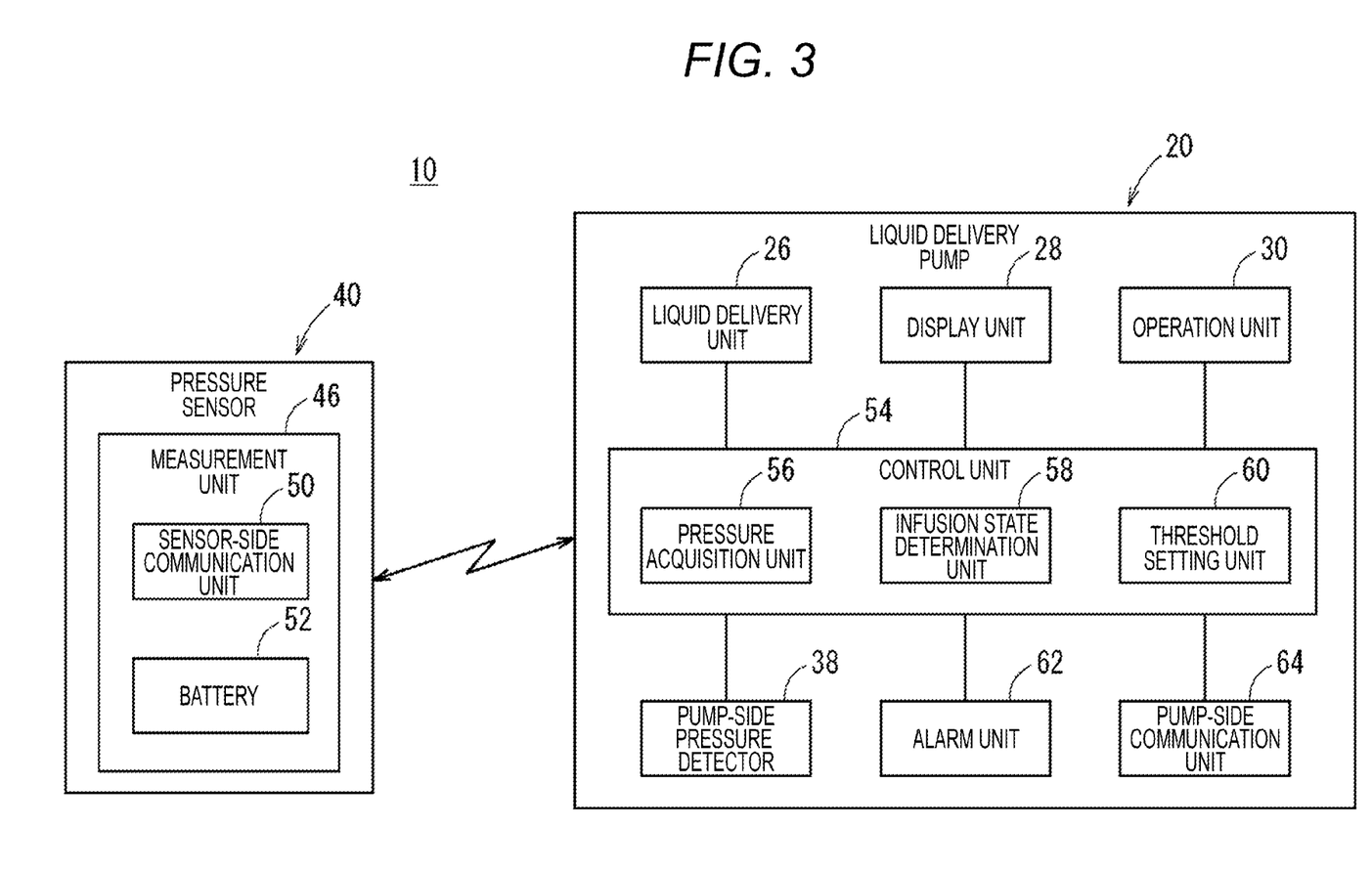
FIG. 3 is an occlusion diagram illustrating a functional unit of the infusion state detection system of FIG. 1.

Moreover, as illustrated in FIG. 3, the liquid delivery pump 20 internally includes a pump-side pressure detector 38 configured to detect the pressure in the conduit 16*a* of the tube 16. The pump-side pressure detector 38 detects the pressure in the conduit 16*a* in the liquid delivery pump 20. The infusion state detection system 10 according to the present embodiment performs specific determination by detecting the pressure using two pressure detectors, that is, the pump-side pressure detector 38 and a pressure sensor 40 to be described below. Note that the infusion state detection system 10 may of course detect the pressure inside the infusion line 12 with solely any one of the pump-side pressure detector 38 and the pressure sensor 40.

Returning to FIG. 1, the infusion state detection system 10 according to the present embodiment is formed by providing the pressure sensor 40 on the infusion line 12 and using the above-described liquid delivery pump 20.

The pressure sensor 40 is provided on the tube 16 close to the indwelling needle 18 in order to detect the pressure inside the infusion line 12 in the vicinity of the discharge position of the medicinal solution L. The pressure sensor 40 includes a disk shape, one surface thereof being fixed to the body surface of the patient C. For example, as illustrated in FIG. 2, the pressure sensor 40 includes a case 44 and a measurement unit 46. The case 44 is attached to the body surface via a tape 42. The measurement unit 46 closes an opening surface of a measurement chamber 44*a* of the case 44 and measures the pressure inside the measurement chamber 44*a*.

The case 44 includes a measurement chamber 44*a*, an inflow port 44*b* and an outflow port 44*c*. The inflow port 44*b* communicates with the measurement chamber 44*a* and is connected to the tube 16 on the upstream side. The outflow port 44*c* communicates with the measurement chamber 44*a* and is connected to the tube 16 on the downstream side. The measurement chamber 44*a* temporarily stores (at a low liquid pressure) the medicinal solution L flowing in from the inflow port 44*b* in the normal state of infusion fluid and allows the medicinal solution L to flow out of the outflow port 44*c*. The measurement chamber 44*a*, the inflow port 44*b*, and the outflow port 44*c* may be configured as a single conduit.

The measurement unit 46 includes a diaphragm 48 on an opposing surface of the measurement chamber 44*a* and detects the pressure of the medicinal solution L that has flown into the measurement chamber 44*a*. That is, the measurement unit 46 detects a low pressure in a case where the diaphragm 48 is hardly deformed in the normal state of the infusion and detects a high pressure in a case where the diaphragm 48 is expanded due to an abnormality in the infusion. Moreover, the measurement unit 46 includes a sensor-side communication unit 50 and a battery 52 (refer to FIG. 3), and wirelessly transmits a pressure detection signal to the liquid delivery pump 20 via the sensor-side communication unit 50.

As illustrated in FIG. 3, the infusion state detection system 10 controls an entire system by a control unit 54 provided in the liquid delivery pump 20. Basically, the control unit 54 controls the liquid delivery unit 26 to deliver the medicinal solution L. The control unit 54 is formed with a known computer (a microcomputer, or the like) including an arithmetic processing unit, a storage unit, and an input/output unit (not illustrated). The control unit 54 drives the squeezing mechanism 36 on the basis of the liquid delivery amount set by the user via the operation unit 30 and delivers the medicinal solution L in the tube 16.

By executing a program of the infusion state detection system 10, the control unit 54 serves as a determination processing unit for determining whether the infusion state is normal or abnormal. More specifically, the control unit 54 internally includes a pressure acquisition unit 56, an infusion state determination unit 58, and a threshold setting unit 60 provided by executing a program. Moreover, an alarm unit 62 is provided in advance in the liquid delivery pump 20 as a functional unit of the infusion state detection system 10.

The pressure acquisition unit 56 is a functional unit that receives a detection signal of the pressure sensor 40 periodically (or by sending a transmission instruction to the pressure sensor 40) and processes this detection signal to obtain a pressure value. The pressure acquisition unit 56 wirelessly receives a detection signal from the sensor-side communication unit 50 by the pump-side communication unit 64 provided in the liquid delivery pump 20. With this configuration, it is possible, in the infusion state detection system 10, to reduce the number of electrical wirings and reduce the work burden at the time of construction of the infusion line 12. Additionally, it is possible to facilitate operation of the patient C even during infusion. The pressure sensor 40 and the control unit 54 may alternatively communicate with each other by wire.

On the basis of the pressure value obtained by the pressure acquisition unit 56, the infusion state determination unit 58 determines whether the infusion state is normal or abnormal. Hereinafter, a principle of determination of the infusion state by the infusion state determination unit 58 will be described.

In the normal state, the infusion line 12 discharges the medicinal solution L from the small outside diametered tube 24 of the indwelling needle 18 inserted into the blood vessel V and allows the medicinal solution L to flow in the blood vessel V (also refer to FIG. 2). In the infusion line 12, however, as described above, the pressure inside the infusion line 12 might increase due to a blood pressure change by a change in the posture of the patient C, a change in venous pressure, or the like (hereinafter, this will be referred to as an increase phenomenon at a normal state).

Figure 4A:
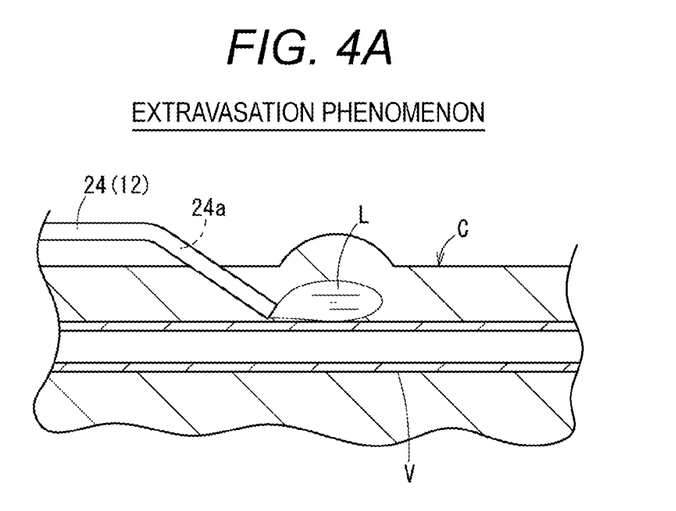
FIG. 4A is a diagram schematically illustrating an extravasation phenomenon.

Moreover, in the infusion line 12, there might be a case where a physical trouble occurs in the infusion line 12 due to some cause during the infusion (for example, physical movement of the patient C, a force acting on the tube 16 and the indwelling needle 18) resulting in a failure of supplying the medicinal solution L normally to the inside of the blood vessel V of the patient C. For example, as illustrated in FIG. 4A, there is a possibility that the tip of the indwelling needle 18 comes out of the blood vessel V and is positioned in the subcutaneous tissue and supplies, in this state, the medicinal solution L (hereinafter referred to as "extravasation phenomenon"). In this case, although the medicinal solution L flows somewhat, the flow of the medicinal solution L is less smooth compared with the normal state. Even in such a state, the liquid delivery pump 20 delivers the liquid at a constant flow rate, and the medicinal solution L partially accumulates inside the infusion line 12. This increases the pressure inside the infusion line 12 until the pressure reaches a pressure needed to carry the medicinal solution L at a flow rate delivered from the liquid delivery pump 20 to the inside of the infusion line 12 that has difficulty in achieving a smooth flow. This leads to an increase in the pressure in the measurement chamber 44a of the pressure sensor 40.

Figure 4B:
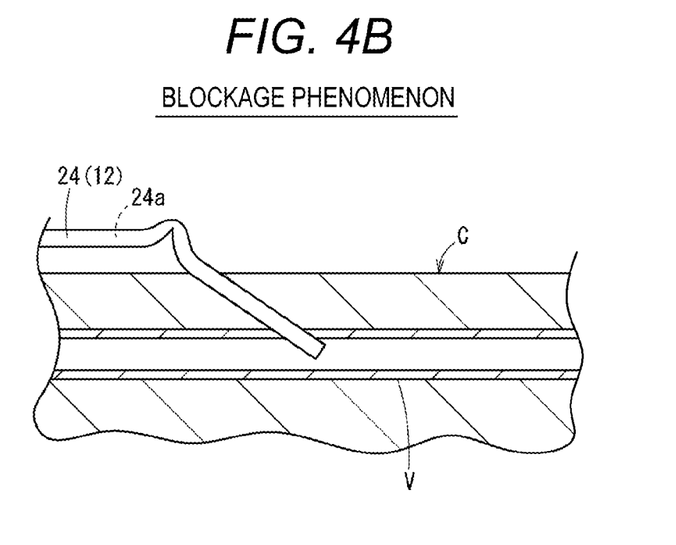
FIG. 4B is a diagram schematically illustrating an occlusion phenomenon.

Moreover, for example, as illustrated in FIG. 4B, there is a possibility that the middle portion of the indwelling needle 18 and the tube 16 is kinked, and the inside of the infusion line 12 is occluded (hereinafter referred to as a occlusion phenomenon). In this case, the conduit 16a and the discharge passage 24a are substantially occluded, prohibiting the flow of the medicinal solution L. Therefore, the medicinal solution L delivered from the liquid delivery pump 20 accumulates inside the infusion line 12, increasing the pressure inside the infusion line 12. This also increases the pressure in the measurement chamber 44a of the pressure sensor 40.

The infusion state determination unit 58 determines whether the infusion state is normal or abnormal in a case where the pressure in the measurement chamber 44a increases due to a plurality of types of causes as described above. Specifically, the liquid delivery stopping threshold Ps (predetermined pressure) is stored in advance in the storage unit, and the pressure value obtained by the pressure acquisition unit 56 is compared with the liquid delivery stop threshold Ps, during the infusion. Subsequently, when the pressure value becomes the liquid delivery stop threshold Ps or above, the driving of the liquid delivery unit 26 is stopped and processing of stopping the delivery of the medicinal solution L inside the infusion line 12 is performed (hereinafter referred to as a liquid delivery stop state).

In this manner, in a case where the liquid delivery pump 20 stops delivering the medicinal solution L, the pressure changes in the measurement chamber 44a. The infusion state determination unit 58 distinguishes between the extravasation phenomenon, and other normal state increase phenomenon or occlusion phenomenon, on the basis of the fluctuation of the pressure value during implementation of the liquid delivery stop state (during the liquid delivery stop period).

Figure 5A:
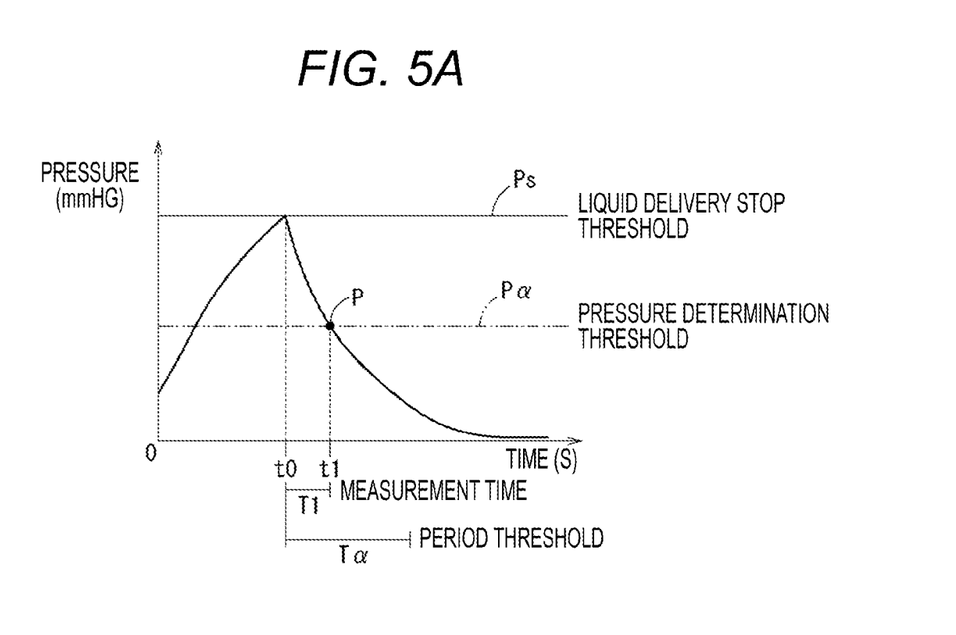
FIG. 5A is a graph illustrating a pressure value change at the time of occurrence of an extravasation phenomenon and a method for determination by a control unit.

Specifically, as illustrated in FIG. 5A, in a case where an extravasation phenomenon occurs in the infusion line 12, the pressure value demonstrates a reaction of a relatively sudden decrease in the liquid delivery stop state. In the case of the extravasation phenomenon, the medicinal solution L flows to the outside of the infusion line 12 although the resistance is high. Accordingly, when the liquid is not delivered from the liquid delivery pump 20, the medicinal solution L accumulated in the infusion line 12 continues to flow out to the subcutaneous tissue on the downstream side of the pressure sensor 40, and the pressure value decreases in a short time.

Figure 5B:
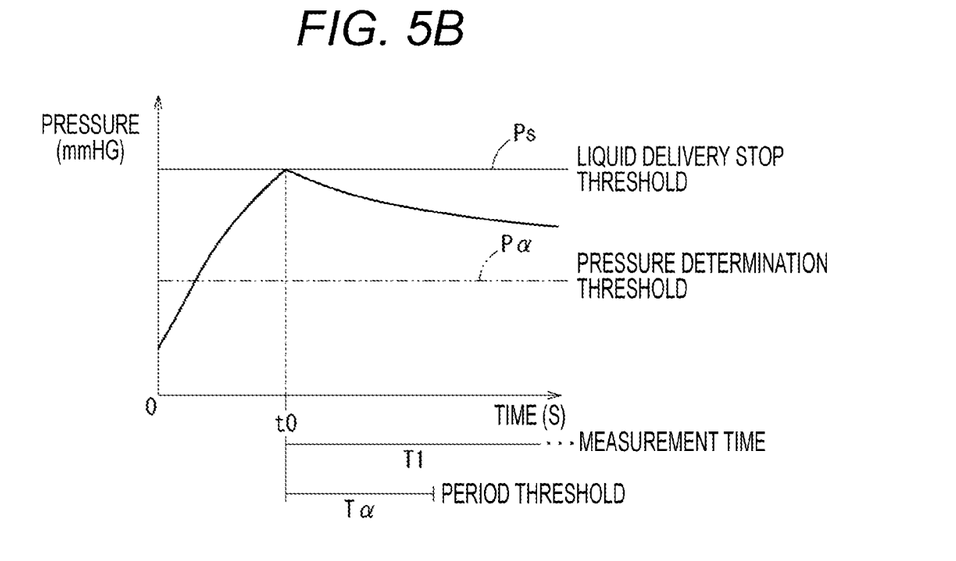
FIG. 5B is a graph illustrating a pressure value change in another phenomenon and a method for determination by the control unit.

In contrast, in a case where an occlusion phenomenon occurs, the medicinal solution L continuously remains in the infusion line 12 even after the stoppage of the liquid delivery from the liquid delivery pump 20. Therefore, the pressure inside the infusion line 12 does not change in principle, but the pressure might gradually decrease due to the flexibility of the tube 16. As illustrated in FIG. 5B, the degree of the pressure decrease at this time is more gradual compared with the case of the extravasation phenomenon illustrated in FIG. 5A. Moreover, in a case of normal administration, there is substantially no pressure increase due to liquid delivery, and the reason for the increase in the pressure inside the infusion line 12 is due to the blood pressure of the patient. That is, in the case of an increase phenomenon at a normal state, the cause is a change in the blood pressure of the patient C, and thus, the pressure inside the infusion line 12 does not change even when the liquid delivery is stopped.

Accordingly, the infusion state determination unit 58 can estimate the occurrence of the extravasation phenomenon by monitoring the change in the pressure value after the liquid delivery stop state. Specifically, as illustrated in FIG. 5A, the infusion state determination unit 58 includes a pressure determination threshold Pα set to a predetermined ratio with respect to the liquid delivery stop threshold Ps, and a preset period threshold Tα. The infusion state determination unit 58 starts measuring the time from the time t0 of becoming the liquid delivery stop state and calculates a measurement time T1 up to the time t1 at which the pressure value reaches the pressure determination threshold Pα.

After calculating the measurement time T1, the infusion state determination unit 58 determines whether the measurement time T1 is longer than the period threshold Tα. As illustrated in FIG. 5A, the determination result that the measurement time T1 is shorter than the period threshold Tα indicates a sudden decrease in the pressure value, and thus, this case is decided to be an extravasation phenomenon. Conversely, as illustrated in FIG. 5B, the determination result that the measurement time T1 is longer than the period threshold Tα indicates that the fluctuation of the pressure value is small, and thus, the case is decided to be not an extravasation phenomenon.

While, in the present embodiment, the pressure determination threshold Pα is set to ½ of the liquid delivery stop threshold Ps, the pressure determination threshold Pα is not limited this value. For example, in a case where the ratio of the pressure determination threshold Pα to the liquid delivery stop threshold Ps is within a predetermined range, for example, ½ to ¾, it is possible to detect the occurrence of an extravasation phenomenon in a relatively short time. While the setting of the period threshold Tα depends on the setting of the pressure determination threshold Pα, it would be preferable to set the period threshold Tα to be in the range of a predetermined time (second), for example, 10 seconds to 30 seconds, because this range enables satisfactory detection of the extravasation phenomenon without extending the stop period of liquid delivery.

Figure 6A:
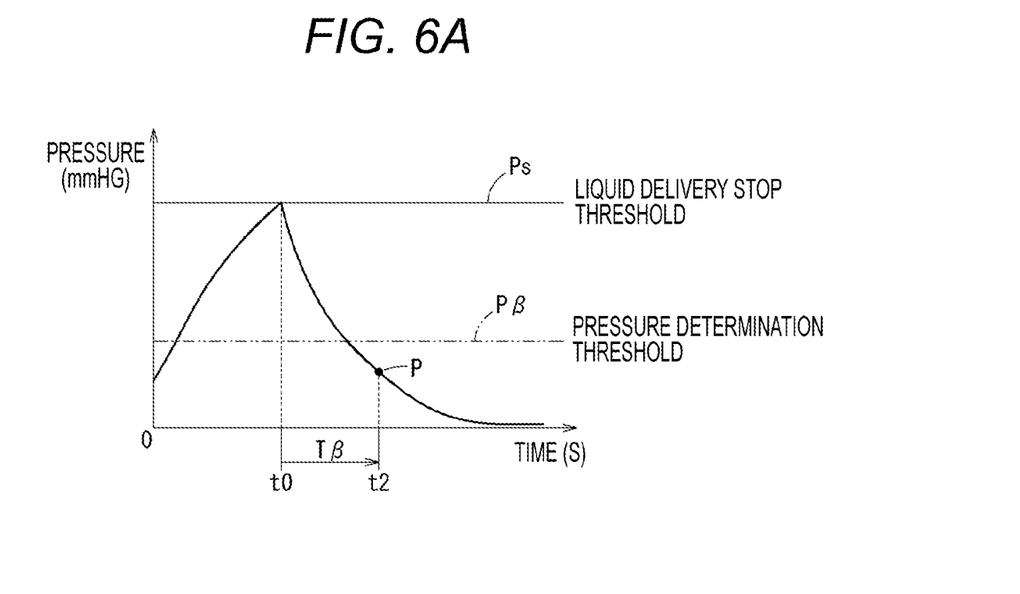
FIG. 6A is a graph illustrating a method for determining an extravasation phenomenon by the control unit according to a first modification.

The determination method by the infusion state determination unit 58 is not limited to the above, and various modifications can be adopted. For example, as illustrated in FIG. 6A, it is allowable to configure such that the infusion state determination unit 58 includes a period threshold Tβ and a pressure determination threshold Pβ, and a pressure value P at a time t2 at which the period threshold Tβ is passed from the time t0 of becoming the liquid delivery stop state is compared with the pressure determination threshold Pβ. In a case where the pressure value P is the pressure determination threshold Pβ or below, the phenomenon is decided as an extravasation phenomenon, and in a case where the pressure value P is larger than the pressure determination threshold Pβ, the phenomenon is decided as not the extravasation phenomenon.

In this manner, by using the pressure value P at the period threshold Tβ, the infusion state detection system 10 can estimate whether the phenomenon is an extravasation phenomenon within a certain period of time. This makes it possible to shorten the liquid delivery stop period.

Figure 6B:
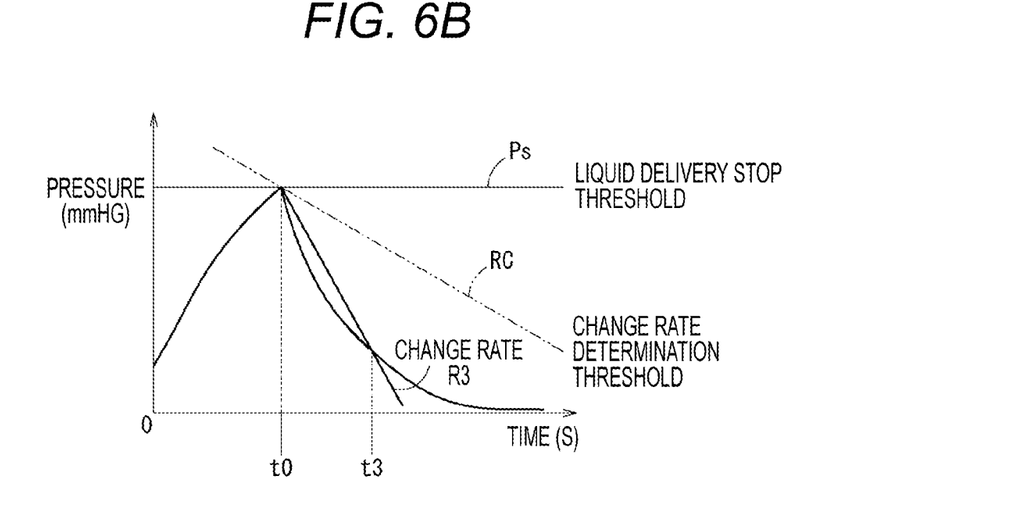
FIG. 6B is a graph illustrating a method for determining an extravasation phenomenon by the control unit according to a second modification.

Moreover, for example, as illustrated in FIG. 6B, it is allowable to configure such that the infusion state determination unit 58 includes a pressure value change rate determination threshold RC, and performs comparison with a change rate R3 for a predetermined time t3 that is passed from the time t0 of becoming the liquid delivery stop state. Subsequently, in a case where the change rate R3 is greater than the change rate determination threshold RC (in a case of abrupt decrease), it is decided that the phenomenon is an extravasation phenomenon, and in a case where the change rate R3 is smaller than the change rate determination threshold RC (in a case of gradual decrease), it is determined that it is not an extravasation phenomenon.

In this manner, the infusion state detection system 10 can also estimate whether the phenomenon is an extravasation phenomenon on the basis of a waveform of a detected pressure value by determining using the change rate of the pressure value. While the predetermined time t3 is not particularly limited, it is preferable to set to the value within a range of 30 seconds from the time t0. With this configuration, it is possible to shorten the liquid delivery stopped period. In addition to the calculation on the basis of the individual pressure values at the time t0 and the time t3, the change rate calculation method may include calculation of performing differentiation at a time close to the time t0. Moreover, the number of times (the number of times) to calculate the change rate is not particularly limited, and by performing for a plurality of numbers of times, it is possible to achieve a higher determination accuracy.

Moreover, other than performing one type of the above-described determination method, the infusion state determination unit 58 may determine the infusion state by combining a plurality of types of determination methods. This further enhances the determination accuracy.

Returning to FIG. 3, in a case where the infusion state determination unit 58 determines that the pressure increase is an extravasation phenomenon, the infusion state determination unit 58 activates the alarm unit 62 and outputs an alarm indicating the occurrence of the extravasation phenomenon. The alarm output by the alarm unit 62 includes the alarm issued by various methods such as alarm sound and voice output. Alternatively, the control unit 54 may display the occurrence of the extravasation phenomenon using the display unit 28. In the display of the display unit 28, is allowable to configure to perform guiding display of a necessary countermeasure for the extravasation phenomenon.

Moreover, the control unit 54 continues to stop driving the liquid delivery unit 26 at the time of determining the extravasation phenomenon. This reduces the leakage of the medicinal solution L to the subcutaneous tissue of the patient C. Furthermore, the control unit 54 is preferably configured to communicate with a management server, or the like, in the hospital to inform the occurrence of the abnormality (extravasation phenomenon) in the infusion.

Moreover, in a case where the infusion state determination unit 58 determines that the pressure increase is not an extravasation phenomenon, the infusion state determination unit 58 drives the liquid delivery unit 26 and restarts delivery of the medicinal solution L. Note that it is preferable to restart the delivery of the medicinal solution L at a time where the period threshold Tα is passed, without waiting until the pressure value reaches the threshold Pα for the pressure determination. With this configuration, it is possible to avoid prolongation of the liquid delivery stop state of the medicinal solution L.

The infusion state determination unit 58 monitors the pressure value detected by the pressure sensor 40 even after the restart of delivery of the medicinal solution L. In a case where the pressure is not increased after the restart of the delivery of the liquid, the pressure increase at this time is estimated to be an increase phenomenon at a normal state, and delivery of the liquid medicinal solution L is continued.

In contrast, in a case where the pressure value increases again with the restart of liquid delivery, the pressure increase at this time is estimated to be an occlusion phenomenon. That is, re-increase of the pressure value can be considered to indicate that the inside of the infusion line 12 is occluded, substantially stopping the medicinal solution flow. In a case where the occlusion phenomenon is estimated, the control unit 54 activates the alarm unit 62 and outputs an alarm, and then, stops driving the liquid delivery unit 26. This makes it possible to deal with the occlusion phenomenon of the infusion line 12 immediately. Note that the alarm for the occlusion phenomenon is different from the alarm for the extravasation phenomenon, thereby enabling the user to separately recognize the individual abnormalities.

Moreover, the threshold setting unit 60 of the control unit 54 includes a function of automatically setting the threshold pressure value Ps for liquid delivery stopping on the basis of the liquid delivery amount of the medicinal solution L. That is, in a case where the liquid delivery amount is small, the rate of increase of the pressure value detected by the pressure sensor 40 also decreases. Accordingly, the threshold setting unit 60 sets a low threshold pressure value Ps for liquid delivery stopping. For example, in a case where the liquid delivery amount is 1 mL/h, the threshold pressure value Ps for liquid delivery stopping is set to around 1.5 mmHg.

Conversely, in a case where the liquid delivery amount is large, the rate of increase of the pressure value detected by the pressure sensor 40 also increases. Accordingly, the threshold setting unit 60 sets a high threshold Ps for liquid delivery stopped. For example, in a case where the liquid delivery amount is 500 mL/h, the threshold pressure value Ps for the liquid delivery stopping is set to around 450 mmHg. Of course, the infusion state detection system 10 may be configured such that the user manually sets the threshold pressure value Ps for liquid delivery stopping.

Figure 7:
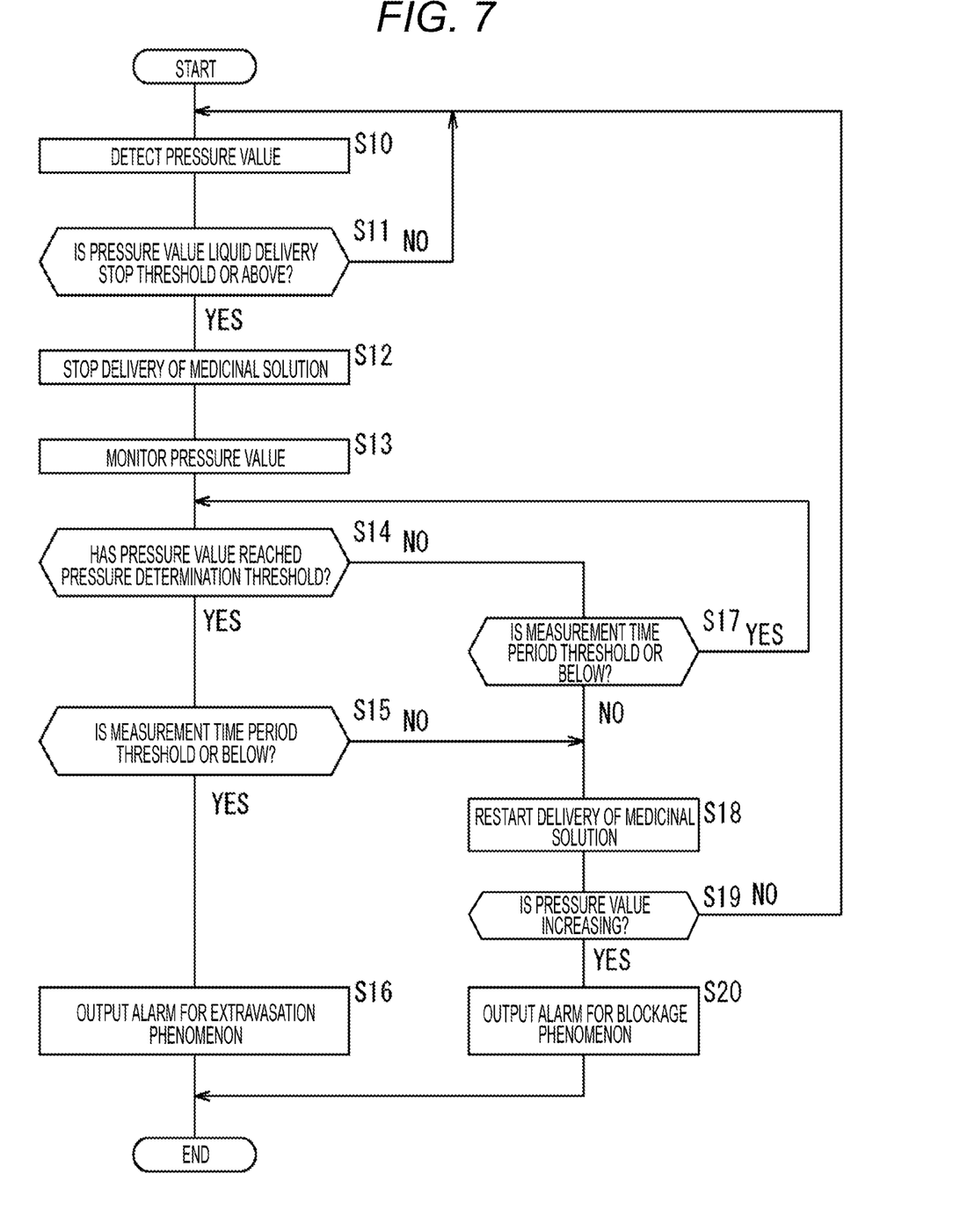
FIG. 7 is a flowchart illustrating a processing flow of the control unit of the infusion state detection system in FIG. 1.

Following the above description on the basic configuration of the infusion state detection system 10 according to the present embodiment, operation and effect thereof will be described below with reference to the flowchart of FIG. 7.

In the infusion state detection system 10, the infusion line 12 including the pressure sensor 40 is formed by the user, and thereafter, the control unit 54 starts driving together with power on of the liquid delivery pump 20. Subsequently, the liquid delivery amount of the medicinal solution L is set by the operation of the operation unit 30 by the user, and then, the threshold setting unit 60 automatically sets the threshold pressure value Ps for liquid delivery stopping. This completes preparation of the infusion state detection system 10 and the infusion line 12, and the control unit 54 starts a processing flow together with the start of the drive of the liquid delivery pump 20 (delivery of medicinal solution L).

After starting the processing flow, the control unit 54 receives a detection signal transmitted by the pressure sensor 40 by the pressure acquisition unit 56 and detects a pressure value at a position in the vicinity of the indwelling needle 18 (step S10).

Subsequently, the control unit 54 compares the detected pressure value with the threshold pressure value Ps set for liquid delivery stopping by the threshold setting unit 60 and determines whether the pressure value is the threshold pressure value Ps for liquid delivery stopping or above (step S11). In a case where the pressure value is lower than the threshold pressure value Ps for liquid delivery stopping, the processing returns to step S10 to monitor the pressure value at the time of delivery of the medicinal solution L. In a case where the pressure value is the threshold pressure value Ps for liquid delivery stopping or above, processing proceeds to step S12.

In step S12, the control unit 54 stops driving the liquid delivery unit 26 and stops delivery of the medicinal solution L. During this stop period, the control unit 54 measures the lapse of time from the time t0 at which the liquid delivery is stopped and monitors the pressure value of the pressure sensor 40 (step S13). Furthermore, during the stop period, the control unit 54 compares the pressure value with the threshold pressure value Pα for pressure determination and determines whether the pressure value has reached the threshold pressure value Pα for pressure determination (step S14). In a case where the pressure value has not reached the threshold pressure value Pα for pressure determination, processing proceeds to step S17.

In a case where the pressure value has reached the threshold pressure value Pα for pressure determination in step S14, the measurement time period T1 is calculated from the time t1, and it is determined whether the measurement time period T1 is the threshold Tα for time period or below (step S15). In a case where the measurement time period T1 is the threshold Tα for time period or below, the processing proceeds to step S16. In a case where the measurement time period T1 is greater than the threshold Tα for time period, processing proceeds to step S18.

In step S16, the control unit 54 decides that an extravasation phenomenon has occurred, and outputs an alarm for the extravasation phenomenon by the alarm unit 62. Moreover, the control unit 54 continues to stop driving the liquid delivery unit 26.

In contrast, in a case where the pressure value has not reached the threshold pressure value Pα for the pressure determination in step S14, the measurement time T1 is calculated in step S17 from the time t1 as in step S15, and it is determined whether the measurement time period T1 the threshold Tα for time period or below. In a case where the measurement time period T1 is the threshold Tα for time period, processing returns to step S14. In a case where the measurement time period T1 is greater than the threshold Tα for time period, processing proceeds to step S18.

In step S18, the control unit 54 decides that no extravasation phenomenon has occurred and ends the stop period, and then, restarts the delivery of the medicinal solution L by the liquid delivery unit 26. At this time, the control unit 54 continues acquisition of the pressure value.

Subsequently, after restarting the liquid delivery, the control unit 54 determines whether the pressure value is increasing (that is, whether it is decreasing or constant) (step S19). In a case where the pressure value is increasing, the control unit 54 estimates that the occlusion phenomenon has occurred and proceeds to step S20. In contrast, in a case where the pressure value is decreased or constant, the control unit 54 estimates the occurrence of an increase phenomenon at a normal state and returns to step S10, and then, continues the delivery of the medicinal solution L and the monitoring of the pressure inside the infusion line 12.

In step S20, the control unit 54 outputs an alarm for occlusion phenomenon by the alarm unit 62. Moreover, the control unit 54 stops driving the liquid delivery unit 26 and stops delivery of the medicinal solution L again. Subsequently, the infusion state detection system 10 finishes this processing flow on the basis of operation by the user after outputting the alarm or during infusion.

As described above, the infusion state detection system 10 according to the present embodiment can satisfactorily estimate the extravasation phenomenon by detecting a sudden decrease in the pressure value during the stop period of the liquid delivery pump 20. Therefore, notification of the occurrence of the extravasation phenomenon to the user by the control unit 54 enables the user to take necessary countermeasures at an early stage. As a result, the infusion state detection system 10 achieves higher reliability of detection and further enhances the usability. Moreover, as a result of this determination processing, it is possible to quantitatively deliver the liquid without changing the liquid delivery amount of the medicinal solution L during infusion, leading to facilitated liquid supply control.

In this case, the control unit 54 measures the time period at which the pressure value inside the infusion line 12 during the stop period reaches a value of the pressure determination threshold or below, thereby detecting the extravasation phenomenon satisfactorily in a case where the measurement time period T1 is the threshold Tα for time period Tα or below. Moreover, in a case where the pressure value increases after restarting the drive of the liquid delivery pump 20, the control unit 54 can estimate that an occlusion phenomenon is occurring. Accordingly, the user can receive a notification of the occurrence of the occlusion phenomenon from the liquid delivery pump 20 and can take necessary measures at an early stage.

Furthermore, the pressure sensor 40 is arranged at a position in the vicinity of the indwelling needle 18 (insertion section) of the infusion line 12, thereby detecting the pressure value inside the infusion line 12 near the indwelling needle 18. With this configuration, it is possible to determine the infusion state by the control unit 54 with higher accuracy. Moreover, the control unit 54 automatically sets the threshold pressure value Ps for liquid delivery stopping on the basis of the liquid delivery amount of the medicinal solution L, it is possible to monitor the pressure change according to the liquid delivery amount, leading to further enhancement of the usability of the infusion state detection system 10.

In the above, certain embodiments have been described. It should be readily apparent however, that the present invention is not intended to be limited to the above-described embodiments but various modifications are possible without departing from the scope of the present invention. For example, estimation of the occlusion phenomenon by the control unit 54 may also use the change rate until the pressure value increases to reach the threshold pressure value Ps for liquid delivery stopping regardless of the pressure value after restarting delivery of the medicinal solution. Specifically, occurrence of occlusion inside the infusion line 12 hinders flow of the medicinal solution L and thus, the pressure value increases relatively suddenly. With this configuration, the control unit 54 can satisfactorily determine the occlusion phenomenon on the basis of the change rate (rate of increase) of the pressure value.

Moreover, the control unit 54 may estimate the infusion state inside the infusion line 12 by using the pump-side pressure detector 38 and the pressure sensor 40 in combination. That is, in a case where there is a significant difference in a change in the pressure value between the pump-side pressure detector 38 and the pressure sensor 40, it is possible to estimate the occurrence of the occlusion phenomenon of the tube 16. Moreover, the pressure value of the pressure sensor 40 may be used for determination of the extravasation phenomenon, and the pressure value of the pump-side pressure detector 38 may be used for determination of the occlusion phenomenon.

The invention claimed is:

1. An infusion state detection system comprising:
    a pump unit configured to deliver a liquid to a patient via an infusion line and an indwelling needle, the pump unit comprising a first pressure detector configured to detect a pressure in the infusion line at a location on a downstream side of the pump unit;
    a second pressure detector configured to be fixed to a body surface of the patient at a position proximate the indwelling needle and configured to detect a pressure inside the infusion line; and
    a determination processing unit configured to:
        when the pressure detected by the first pressure detector or the second pressure detector is at a predetermined pressure value or above, stop driving of the pump unit for a stop period,
        determine an infusion state on the basis of a value of the pressure in the infusion line detected by the first pressure detector and a value of the pressure in the infusion line detected by the second pressure detector during the stop period,
        determine that occlusion of the infusion line has occurred based on a difference between (i) a change in the value of the pressure in the infusion line detected by the first pressure detector and (ii) a change in the value of the pressure in the infusion line detected by the second pressure detector, and
        determine that leakage of the liquid to an outside of a living body lumen has occurred based on the value of the pressure in the infusion line detected by the second pressure detector.

2. The infusion state detection system according to claim 1,
    wherein the determination processing unit is configured to:
        determine a time period, from commencement of the stop period, at which a ratio of the value of the pressure in the infusion line detected by the second pressure detector to the predetermined pressure value is at a predetermined ratio or below, and
        determine that leakage of the liquid to an outside of a living body lumen has occurred when the determined time period is a predetermined time period threshold or below.

3. The infusion state detection system according to claim 1,
    wherein the determination processing unit is configured to:
        determine the value of the pressure in the infusion line detected by the second pressure detector at a time when a predetermined time period threshold has passed from commencement of the stop period, and
        determine that leakage of the liquid to an outside of a living body lumen has occurred when the value of the pressure in the infusion line detected by the second pressure detector at the time when the predetermined time period threshold has passed from commencement of the stop period is at a predetermined threshold value or below.

4. The infusion state detection system according to claim 1,
    wherein the determination processing unit is configured to:
        determine a change rate of the value of the pressure inside the infusion line detected by the second pressure detector during the stop period, and
        determine that leakage of the liquid to an outside of a living body lumen has occurred when the change rate is at a predetermined threshold rate or above.

5. The infusion state detection system according to claim 1,
    wherein the determination processing unit is configured to determine that occlusion of the infusion line has occurred when driving of the pump unit is restarted after the end of the stop period and the value of the pressure detected by the first pressure detector or the second pressure detector increases after the restart.

6. The infusion state detection system according to claim 1,
    wherein the determination processing unit is configured to automatically set the predetermined pressure value on the basis of a liquid delivery amount of the pump unit.

* * * * *